United States Patent [19]

Kersten et al.

[11] Patent Number: 4,599,467
[45] Date of Patent: Jul. 8, 1986

[54] PRODUCTION OF VICINAL ALKYLENE GLYCOLS

[75] Inventors: Hilde Kersten, Erlenbach; Gerhard Meyer, Obernburg, both of Fed. Rep. of Germany

[73] Assignee: AKZO NV, Arnhem, Netherlands

[21] Appl. No.: 722,180

[22] Filed: Apr. 10, 1985

Related U.S. Application Data

[63] Continuation of Ser. No. 589,452, Mar. 12, 1984, abandoned, which is a continuation-in-part of Ser. No. 374,609, Apr. 30, 1982, abandoned, which is a continuation of Ser. No. 175,205, Jul. 31, 1980, abandoned.

[30] Foreign Application Priority Data

Aug. 4, 1979 [DE] Fed. Rep. of Germany ....... 2931753

[51] Int. Cl.$^4$ .................. C07C 29/00; C07C 29/78
[52] U.S. Cl. ................................ 568/867; 260/413; 568/672; 568/822; 568/844; 568/856; 568/868
[58] Field of Search ....................... 568/867, 858

[56] References Cited

U.S. PATENT DOCUMENTS 3,629,343  12/1971  Levin et al. .......................... 568/867

FOREIGN PATENT DOCUMENTS 2141470  2/1973  Fed. Rep. of Germany ...... 568/867
2023601  1/1980  United Kingdom ................ 568/867

*Primary Examiner*—J. E. Evans
*Attorney, Agent, or Firm*—Michael J. Striker

[57] ABSTRACT

A process is provided for production of vicinal alkylene glycols by hydrolysis of an epoxyalkane having from 6 to 24 carbon atoms in the presence of water and a basic catalyst and under carbon dioxide pressures of from 100 to 300 bars and temperatures of from about 200° C. to 350° C. Also disclosed are homogeneous mixtures of epoxyalkanes and/or vicinal alkylene glycols having from 6 to 24 carbon atoms, water, a basic catalyst and carbon dioxide in an amount corresponding to a carbon dioxide partial pressure of from about 100 to 300 bars, provided at temperatures from about 200° C. to 350° C. The process provides high yields, selectivities and reaction velocities and the resulting products are of high purity.

8 Claims, No Drawings

PRODUCTION OF VICINAL ALKYLENE GLYCOLS

This application is a continuation of application Ser. No. 589,452, filed Mar. 12, 1984, which is a continuation-in-part of application Ser. No. 374,609, filed Apr. 30, 1982, which is in turn a continuation of application Ser. No. 175,205, filed July 31, 1980, all abandoned.

BACKGROUND OF THE INVENTION

1. Field of the Invention

This invention relates to a method for producing chain internal and/or end positioned vicinal alkylene glycols having from 6 to 24 carbon atoms by hydrolyzing a corresponding epoxyalkane at elevated temperature and pressure.

2. Brief Description of the Background of the Invention Including Prior Art

According to older known processes, alkylene oxides are heated in the presence of a catalyst with a large excess of water. The excess of water prevents in fact the undesired formation of di-, tri- and polyalkyleneglycols, but results in the disadvantage that only alkyleneglycol solutions of low concentration are obtained. For the technical preparation of vicinal glycols these proceses are less suitable, since the work up of the low concentration glycol solutions requires a lot of energy and a high expenditure for equipment. In addition, the yields amount to only about 90 percent of theory even with comparably long reaction times.

More recent processes are also known providing without or with small water excess yields of about 97 percent.

According to a process disclosed in German Offenlegungsschrift DE-OS 17 93 247, which corresponds to U.S. Pat. No. 3,629,343, alkylene oxides, especially ethylene oxide and propylene oxide, are hydrolyzed in the presence of carbon dioxide under a pressure of from 10 to 180 bar and at a temperature from 80° to 220° C. in the presence of an alkali metal halogenide or of a quaternary ammonium compound as a catalyst. The alkylene oxide, water and carbon dioxide form initially an alkylene carbonate, which then with water forms the desired vicinal glycol after splitting off of carbon dioxide. Preferably, this hydrolysis is performed in the presence of basic compounds, for example carbonates, bicarbonates or alkali metal hydroxides, in order to decrease the formation of dialkylene glycols and to accelerate the process.

Disadvantages of the process include comparatively long reaction times and the fact that the required catalyst cannot be completely separated from the reaction product. The content of halides present in the glycols is so large that they are unsuitable for certain applications. In addition, this known process shows no advantage when higher, water-insoluble epoxides are employed regarding the yield, since the reaction is performed in heterogeneous phases. Accordingly, a continuous reaction of higher alkylene oxides cannot be considered herein.

A process improved specifically with regard to the preparation of ethylene glycol is described in the German Offenlegungsschrift DE-OS 21 41 470. Instead of the halogen compounds, the catalysts used are alkali salts of aliphatic, alicyclic or one or more ring aromatic mono- or dicarboxylic acids as well as aliphatic or aromatic hydroxycarboxylic acids.

From the German Offenlegungsschriften DE-OS 21 09 453 and 22 03 806 a process is known for the preparation of chain internal, end positioned or cyclical vicinal glycols with from 8 to 30 carbon atoms. The water insoluble epoxides are split in the presence of alkaline acting compounds with strong agitation at temperatures of from 150° C. to 300° C. under the pressures thereby produced (about 30 to 60 bar). Alkali hydroxides are herein employed as alkaline acting compounds. It is a disadvantage of this process that the reaction occurs between heterogeneous phases and that intense mixing of the reaction mixture is required. Since in addition, reaction times of from half an hour to two hours are required, this process is not suitable for the technical continuous production of higher vicinal glycols.

Furthermore, the German Offenlegungsschrift DE-OS 22 56 907 discloses a process for the production of vicinal glycols wherein the hydrolysis is performed with aqueous solutions of salts of aliphatic mono- and/or polycarboxylic acids at temperatures above 100° C. and preferably from 200° C. to 300° C. and if desired in the presence of a solubilizer. The hydrolysis is performed in 1 to 20 percent and preferably 2 to 5 weight percent salt solutions. The solubilizer, which is preferably a water soluble ketone or a cyclical ether such as acetone, dioxane and/or dioxolane is employed in an amount of from 0.5 to 2 parts by weight per weight part of epoxide. In fact this process provides in part fairly good yields and short reaction times, however also in this process the reaction mixture has to be agitated. It is another disadvantage of this process that comparatively expensive auxiliary materials are required.

SUMMARY OF THE INVENTION

1. Purposes of the Invention

It is an object of the present invention to provide a process for preparing vicinal higher glycols, which does not require the application of expensive catalysts or solubilizers, no mechanical agitation of the reaction mixture and no extended reaction times.

It is another object of the present invention to provide a process for preparing vicinal higher glycols suitable for continuous operation.

These and other objects and advantages of the present invention will become evident from the description which follows.

2. Brief Description of the Invention

The present invention provides a method for producing vicinal alkylene glycols by contacting water, a basic catalyst and a compound of the formula

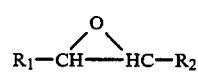

wherein $R_1$ or $R_2$ are the same or different and are each hydrogen $C_nH_{2n+1}$ wherein n is an integer from 1 to 22 and which $C_nH_{2n+1}$ group can be straight chain or branched chain; and $C_nH_{2n-1}$ wherein n is an integer from 1 to 22 and which $C_nH_{2n-1}$ group comprises one aliphatic ring;

and wherein from O to n hydrogen atoms of the $C_nH_{2n\pm1}$ group are substituted by carboxy, halo, alkoxy with from 1 to 6 carbon atoms, hydroxy and heterocyclics;

with the proviso that the sum of the carbon atoms of $R_1$ and $R_2$ together is from 4 to 22. The contacting is performed at temperatures of from about 200° to 350° C. and under a carbon dioxide pressure of from about 100 bar to 300 bar. Preferably the contacting temperature is from about 250° C. to 280° C. Preferred starting materials include those where $R_1$ is hydrogen and where $R_2$ is a straight chain alkyl group of from 4 to 22 carbon atoms. Other preferred starting materials include those where $R_1$ and $R_2$ are straight chain alkyl groups of from 1 to 21 carbon atoms. Preferred starting materials can have from about 12 to 24 carbon atoms in the epoxide molecule.

The above process is characterized versus conventional methods not only by higher yields, selectivities and increased reaction velocities, but also by the purity of the products obtained.

Higher vicinal glycols are valuable compounds and are employed technically as intermediates for organic synthesis of lubricants, ointment bases, coatings, platicizers and foam stabilizers.

DETAILED DESCRIPTION OF THE PREFERRED EMBODIMENTS

In accordance with the present invention it was surprisingly found that higher vicinal glycols can be obtained without the application of expensive catalysts and solubilizers as well as without mechanical agitation of the reaction mixture and with short reaction times. A method is provided for preparing vicinal alkylene glycols by hydrolysis of an epoxyalkane having from 6 to 24 carbon atoms with water under increased temperature and under increased pressure in the presence of carbon dioxide and of a basic catalyst wherein the hydrolysis is performed at temperatures from about 200° to 350 ® C. and under $CO_2$ pressures of from 100 to 300 bar.

The method of the present invention can be employed both with epoxyalkanes wherein the epoxy group is chain internal or end positioned.

The hydrocarbon groups can also be branched and/or carry inert substituents such as for example halogen atoms, ether groups, carboxyl groups or heterocyclic groups. Also, the epoxide mixtures obtainable from the epoxidation of olefins can be employed. Examples of suitable epoxides include 1,2-epoxyhexane, 1,2-epoxyoctane, 3,4-epoxyoctane, 1,2-epoxydecane, 1,2-epoxyhexadecane, 1,2-epoxyoctadecane, 1,2-epoxyheptadecane, as well as mixtures of these epoxyalkanes such as for example $C_{15}$–$C_{16}$ or $C_{15}$–$C_{18}$ mixtures of 1,2-epoxides. Other examples of epoxides include 9,10-epoxy hexadecanoic acid, 1,2-epoxy-3-cyclohexylpropane, 1,2-epoxy-3-isopropylpropane, 1,2-epoxy-6-chlorohexane, 1,2-epoxy-3-hexoxy-hexane, 9,10-epoxy- and 9,10-epoxy-hexadecane.

Useful as basic catalysts are basic compounds which are substantially stable under the reaction conditions. The basic catalysts include compounds such as carbonates, bicarbonates and hydroxides of the alkali and alkaline earth metals, and sodium and potassium are preferred metals. Preferred catalysts are sodium carbonate and sodium bicarbonate. The basic catalyst is employed in an amount of from 0.1 to 5 weight percent and preferably from 0.1 to 2 weight percent relative to the mixture of alkylene oxide and water.

The amount of water employed in the process of the present invention is not critical. A preferred amount of water can be from about 1 to 10 times the weight of the epoxide employed and a more preferred range is from 3 to 8 times the weight of the epoxide employed. Based on the contents in carbon dioxide, the reaction mixture forms a homogeneous phase under the reaction conditions. In the case of alkylene glycols having 8 carbon atoms, the reaction mixture separates after the removal of carbon dioxide into two easily separable phases. The aqueous phase containing the basic catalyst can, if desired, be recirculated, possibly after an extraction process with ether.

It is important in the present invention that the hydrolysis be performed under a relatively high carbon dioxide pressure of from about 100 to 300 bar. It was surprisingly found that under these conditions a homogenization of the reaction mixture occurs.

The hydrolysis temperature is at least 200° C. and preferably above 250° C. and below 280° C. Hydrolysis temperatures of more than 350° C. are to be avoided for economic reasons and because of side and decomposition reactions of the materials employed in the reaction.

As a result of this homogeneity of the reaction mixture, a considerable increase in the reaction velocity and selectivity is achieved. Whereas the conventional processes require reaction times from a half to two hours, in the process of the present invention the reaction is substantially completed after a few minutes. Usually the reaction times are from about 5 to 30 minutes. Practically complete epoxide conversions are obtained, and 98 to 100 percent glycol selectivities are reached.

Another substantial advantage of the present invention is that it is not necessary to constantly agitate the reaction mixture. Thus, the execution of the process of the present invention is substantially more simple than that of the conventional methods. Since, in addition, the reaction times are very short, the application of the inventive process allows one to hydrolyze higher, water insoluble epoxyalkanes into the corresponding vicinal glycols on a large technical scale and in a continuous process, for example, in a tube reactor.

The process of the present invention is performed as a discontinuous process preferably by placing the epoxyalkane, water and the basic catalyst in a pressure reactor, and then by feeding in carbon dioxide in such an amount that the desired pressure is obtained after the desired reaction temperature is reached. In the continuous version of the process of the present invention, for example, the mixture of epoxyalkane, water and the basic catalyst together with the carbon dioxide is passed through the tube reactor under the conditions indicated. The materials remain in the reactor for a time at least sufficient to substantially transform the epoxide into the vicinal glycol.

The vicinal alkylene glycol is obtained after separation of the carbon dioxide and of the aqueous phase. Alkylene glycols soluble in water such as hexanediol-1,2 are separated from the aqueous phase by extraction with ether.

For the purpose of giving those skilled in the art a better understanding of the invention, a preferred procedure for carrying the invention into practice will be set forth by way of example.

EXAMPLES

Initially, the epoxy compound is combined with the three to five fold weight amount of a 5 weight percent aqueous soda ash or sodium carbonate solution in a stainless steel autoclave.

After closing of the autoclave, an amount of carbon dioxide is fed in as to provide at the desired temperature the pressure indicated in Table 1.

For example in a 100 ml Thiedig-autoclave after charging with 5 g 1,2-epoxy-decane, 5 ml of weight percent $NaHCO_3$ aqueous solution and 20 g $CO_2$, a gauge pressure of 130 atmospheres is reached at 250° to 260° C. Employing a 2 liter lift agitate autoclave, after charging of 180 g 1,2-epoxyoctadecane, 750 ml of a 5 weight percent $NaHCO_3$, aqueous solution and of 450 g $CO_2$, a gauge pressure of 240 atmospheres is present at 250° C.

Next the mixture is heated to the temperature indicated in Table 1 and the charge is reacted for the time indicated in Table 1. Then the charge is cooled to about 100° C. and the depressurization of the carbon dioxide is started with further cooling to room temperature at normal pressure. Thereafter the two layers of the example in case are separated, and the aqueous phase is extracted with ether, if desired. Without further purification, products are obtained by this process which have a purity of 94 percent as determined with the diol determination method using $HIO_4$. Higher purities can be obtained by recrystallization with n-hexane.

Although certain preferred embodiments have been disclosed for the purpose of illustration, it will be evident that various changes and modifications may be made without departing from the scope and spirit of the invention.

TABLE 1

| Example | Starting material | Weight ratio epoxide: $H_2O$ | Reaction temper. (°C.) | Pressure at reaction temper. (at gauge) | Reaction time (minutes) | Conversion (%)* | Selectivity (%) | MP (°C.) of the alkyleneglycol raw product |
|---|---|---|---|---|---|---|---|---|
| 1 | 1,2-epoxydecane | 1:5 | 250 | 130 | 15 | 100 | 97 | 45–46 |
| 2 | 1,2-epoxydodecane | 1:4.2 | 250 | 120 | 20 | 98 | 98 | 58–60 |
| 3 | 1,2-epoxyoctadecane | 1:4.2 | 270 | 240 | 25 | 97 | 94 | 76–77 |
| 4 | 1,2-epoxyeicosane | 1:5 | 285 | 270 | 25 | 96 | 94 | 82–83 |
| 5 | Chain internal epoxyhexadecane mixture | 1:5 | 250 | 220 | 15 | 100 | 92 | undetermined |

Undetermined relates to products which do not crystallize well.
*yield = conversion × selectivity × $10^{-2}$

What is claimed is:
1. A method for producing vicinal alkylene glycols having 10 to 24 carbon atoms which comprises:
   contacting in a homogeneous phase at temperatures from about 200° C. to 350° C. and under a carbon dioxide pressure of from about 100 to 300 bar;
   water;
   a catalyst which is solely a basic catalyst selected from the group consisting of carbonates, bicarbonates, and hydroxides of alkali and alkali earth metals; and
   a compound of the Formula (I)

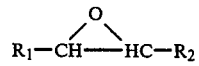

wherein $R_1$, $R_2$ and —CH—CH— form together a straight chain with 10 to 24 carbon atoms, $R_1$ is hydrogen, and $R_2$ is an alkyl group or $R_2$ is hydrogen and $R_1$ is an alkyl group or both $R_1$ and $R_2$ are alkyl groups to form a homogeneous phase mixture containing the alkylene glycol.

2. The method defined in claim 1 wherein the temperature is from 250° C. to 280° C.

3. The method defined in claim 1 wherein $R_1$ is hydrogen and $R_2$ is an alkyl group of 8 to 22 carbon atoms.

4. The method defined in claim 1 wherein the compound of the Formula (I) contains 12 to 24 carbon atoms.

5. The method defined in claim 1 wherein the compound of the Formula (I) is selected from the group consisting of 1,2-epoxydecane, 1,2-epoxyhexadecane, 1,2-epoxyoctadecane, 1,2-epoxyheptadecane, and mixtures thereof.

6. The method defined in claim 1 further comprising the steps of:
   removing carbon dioxide from the homogeneous phase mixture to form two easily separable phases, one of said phases being an aqueous phase containing the basic catalyst; and
   separating the aqueous phase containing the basic catalyst from the remaining phase.

7. A method for producing a vicinal alkylene glycol selected from the group consisting of 1,2-decanediol, 1,2-dodecanediol, 1,2-octadecanediol, and 1,2-eicosanediol respectively, which comprises:
   contacting in a homogeneous phase at a temperature of 250° C. to 280° C. and under a carbon dioxide pressure of 120 to 270 bar;

water;
a catalyst which is solely an alkali metal bicarbonate; and
an epoxy which is respectively 1,2-epoxydecane, 1,2-epoxydodecane, 1,2-epoxyoctadecane or 1,2-epoxyeicosane, to form a homogeneous phase mixture containing the respective vicinal alkylene glycol.

8. The method defined in claim 7 further comprising the steps of:
removing carbon dioxide from the homogeneous phase mixture to form two easily separable phases, one of said phases being an aqueous phase containing the alkali metal bicarbonate catalyst; and
separating the aqueous phase containing the alkali metal bicarbonate from the remaining phase.

* * * * *